(12) United States Patent
Kuemin et al.

(10) Patent No.: US 9,995,700 B2
(45) Date of Patent: Jun. 12, 2018

(54) HEATER STRUCTURE FOR A SENSOR DEVICE

(71) Applicant: Sensirion AG, Stafa (CH)

(72) Inventors: Cyrill Kuemin, Rapperswil (CH); Lukas Buergi, Zurich (CH); Nicolas Moeller, Stafa (CH)

(73) Assignee: Sensirion AG, Stafa (CH)

( * ) Notice: Subject to any disclaimer, the term of this patent is extended or adjusted under 35 U.S.C. 154(b) by 255 days.

(21) Appl. No.: 14/797,369

(22) Filed: Jul. 13, 2015

(65) Prior Publication Data

US 2016/0011134 A1    Jan. 14, 2016

(30) Foreign Application Priority Data

Jul. 14, 2014    (EP) .................................... 14002419

(51) Int. Cl.
| | | |
|---|---|---|
| *H05B 3/68* | (2006.01) | |
| *H05B 3/16* | (2006.01) | |
| *G01N 27/12* | (2006.01) | |
| *H05B 3/00* | (2006.01) | |
| *H05B 3/06* | (2006.01) | |
| *H05B 3/22* | (2006.01) | |
| *G01N 27/14* | (2006.01) | |

(52) U.S. Cl.
CPC ......... *G01N 27/123* (2013.01); *G01N 27/128* (2013.01); *G01N 27/14* (2013.01); *H05B 3/0014* (2013.01); *H05B 3/06* (2013.01); *H05B 3/22* (2013.01); *H05B 3/68* (2013.01)

(58) Field of Classification Search
CPC .... G01N 27/123; G01N 27/128; G01N 27/14; H05B 3/0014; H05B 3/06; H05B 3/22; H05B 3/68

USPC ............................ 219/443.1–468.2, 542–548
See application file for complete search history.

(56) References Cited

U.S. PATENT DOCUMENTS 3,813,520 A * 5/1974 Brouneus ............... H05B 3/265
219/466.1
5,396,047 A * 3/1995 Schilling ............... F24C 15/106
219/448.11

(Continued)

FOREIGN PATENT DOCUMENTS

| CN | 102256387 | 11/2011 |
|---|---|---|
| EP | 2278308 | 1/2011 |

(Continued)

OTHER PUBLICATIONS

Chengxiang Wang et al., "Metal Oxide Gas Sensors: Sensitivity and Influencing Factors", Sensors ISSN 1424-8220, 2010, pp. 2088-2106.

(Continued)

*Primary Examiner* — Sang Y Paik
(74) *Attorney, Agent, or Firm* — Cooper & Dunham LLP (57) ABSTRACT

The sensor device comprises a hotplate on a membrane. The hotplate is heated by a N-fold rotationally symmetric heater structure having N>1 heater elements of identical design. Each heater element comprises an inner section, an intermediate section and an outer section arranged in series, with the inner section having a larger electrical cross section than the outer section. This design allows to heat the hotplate to a homogeneous temperature at moderate supply voltages.

24 Claims, 5 Drawing Sheets

(56) References Cited

U.S. PATENT DOCUMENTS

| | | | | |
|---|---|---|---|---|
| 5,644,676 | A * | 7/1997 | Blomberg | G01J 5/522 219/544 |
| 7,849,727 | B2 * | 12/2010 | Gardner | G01N 33/0031 73/31.06 |
| 2004/0075140 | A1 * | 4/2004 | Baltes | G01N 27/12 257/347 |
| 2014/0208830 | A1 | 7/2014 | Buhler et al. | |

FOREIGN PATENT DOCUMENTS

| | | |
|---|---|---|
| EP | 2278309 | 1/2011 |
| EP | 2778667 | 9/2014 |
| GB | 2422017 | 7/2006 |
| GB | 2464016 | 7/2010 |
| WO | 9519563 | 7/1995 |
| WO | 2014012948 | 1/2014 |

OTHER PUBLICATIONS

Y. Li et al., "Monolithic CMOS Multi-Transducer Gas Sensor Microsystem for Organic and Inorganic Analytes", ScienceDirect, Sensors and Actuators B 126, 2007, pp. 431-440.

G. Muller et al., "A MEMS Toolkit for Metal-Oxide-Based Gas Sensing Systems", ScienceDirect, Thin Solid Films 436, 2003, pp. 34-45.

I. Elmi et al., "Optimization of a Wafer-Level Process for the Fabrication of Highly Reproducible Thin-Film MOX Sensors", ScienceDirect, Sensors and Actuators B 131, 2008, pp. 549-555.

T. Iwaki et al., "Design and Simulation of Resistive SOI CMOS Micro-Heaters for High Temperature Gas Sensors", Institute of Physics Publishing, Journal of Physics: Conference Series 15, 2005, pp. 27-35.

Joseph Watson et al., "The Tin Dioxide Gas Sensor", Meas. Sci. Technol., vol. 4, (1993), pp. 711-719.

M. Baroncini et al., "Thermal Characterization of a Microheater for Micromachined Gas Sensors", ScienceDirect, Sensors and Actuators, A 115 2004, pp. 8-14.

M. Graf, et al., "Smart Single-Chip CMOS Microhotplate Array for Metal-Oxide-Based Gas Sensors", The 12th International Conference on Solid State Sensors, Acuator and Microsystems, Boston, Jun. 8-12, 2013, pp. 123-126.

M. Graf et al., CMOS Microhotplate Sensor System for Operating Temperatures up to 500° C., Elsevier Sensors and Actuators B 117, 2006, pp. 346-352.

R.E. Cavicchi et al., Microhotplate Gas Sensor Arrays, Part of the SPIE Conference on Chemical Microsensors and Applications II, Boston, Massachusetts, Sep. 1999, SPIE vol. 3857, 0277 786X99, pp. 38-49.

P. Ruther et al., "Dependence of the Temperature Distribution in Micro Hotplates on Heater Geometry and Heating Mode", the 12th International Conference on Solid State Sensors, Actuators and Microsystems, Boston, Jun. 8-12, 2003, pp. 73-76.

S.M. Lee et al., "Design and Optimisation of a High-Temperature Distribution in Micro-Hotplate for Nanoporous Palladium Pellistors", Elsevier, Microelectronics Journal 34, 2003, 115-126, pp. 115-126.

S.Z. Ali et al., "High Temperature SOI CMOS Tungsten Micro-Heaters", IEEE Sensors, 2006, EXCO, Daegu, Korea, Oct. 22-25, 2006, pp. 847-850.

Usman Khan et al., "Micro-hot-plates Without Simply Connected Hot-spots and with almost-circular Temperature Distribution", Elsevier Sensors and Actuators B 185 2013, pp. 274-284.

* cited by examiner

HEATER STRUCTURE FOR A SENSOR DEVICE

CLAIM OF PRIORITY

The present patent application claims priority of European patent application 14002419, filed Jul. 14, 2014, the disclosure of which is incorporated herein in its entirety.

Technical Field

The invention relates to a sensor device comprising a substrate with a hotplate and a heater structure arranged in the hotplate.

Background Art

Various types of sensors require elevated temperatures for operation. For example, gas sensors with metal oxide sensing structures best operate at temperatures in a range of at least 100° C. or higher, depending on the oxide to be used and on the gas species to be measured. A gas sensor of this type is described in EP 2278308 or WO 2014/012948.

In order to keep the temperature distribution on the hotplate homogeneous, the heating structure of these devices is a "double spiral" that has wider leads in the central region of the hotplate than in the peripheral, outer region of the hotplate.

DISCLOSURE OF THE INVENTION

The problem to be solved by the present invention is to provide a sensor device of the type mentioned above that has improved versatility.

This problem is solved by the sensor device of claim 1. This device comprises:

- A substrate having a hotplate: The hotplate is the heated area of the device and it has an inner region and an outer region, with the outer region surrounding the inner region.
- A heater structure arranged in said hotplate: The heater structure is structured and adapted for heating the hotplate.
- A driver for generating a heating current through said heater structure: This driver is typically an electrical circuit adapted to generate an electrical current in the heater structure. The driver can be integrated on the substrate or it can be implemented as an external component.
- A sensing structure arranged on said heater structure: This is the sensitive structure of the sensor device, which has to be heated to an elevated temperature.

The heater structure comprises a number N>1 of heater elements, with each of said heater elements having an outer section and an inner section. The outer and inner sections of each heater element are arranged electrically in series. The driver is structured and adapted to heat the heater elements with parallel currents, i.e. with separate currents branched from the same voltage source. In a simple embodiment, this can e.g. be achieved by statically wiring the heater elements to be electrically parallel to each other.

Further, the maximum electrical cross section of the outer section of each heater element is smaller than the maximum electrical cross section of its inner section. In other words, for a given current flowing through the heater element, the current density in the outer section is larger than in the inner section.

The outer sections of the heater elements are arranged in the outer region of said hotplate and the inner sections are arranged in the inner region of said hotplate, i.e. the outer sections are arranged towards the periphery of the hotplate, while the inner sections are arranged towards its center. Since the current densities in the outer sections are larger than in the inner section, this design allows to generate more heat in the periphery of the hotplate, which is required for a uniform temperature distribution. On the other hand, providing several heater elements that can be heated by parallel currents allows to adapt the heater structure to the specific requirements in a more versatile manner. In particular, this design is well suited for low-voltage applications.

Geometrically, the hotplate is advantageously divided into N segments, with N corresponding to the number of heater elements. Each segment extends from the center of the hotplate to the periphery thereof. Further, each segment has an "inner segment region" defined as the intersection between the segment and the inner region of the hotplate, as well as an "outer segment region" defined as the intersection between the segment and the outer region of the hotplate.

In this case, the inner section of each heater element is arranged in one of said inner segment regions, with each inner segment region receiving the inner section of exactly one heater element. Similarly, the outer section of each heater element is arranged in one of said outer segment regions, with each outer segment region receiving the outer section of exactly one heater element.

This design allows to evenly distribute the inner and/or outer heater sections over the hotplate.

The outer section of each heater element can be arranged in a segment different from the inner section of the same heater element. Alternatively, the outer section of each heater element can be arranged in the same segment as the inner section of the same heater element.

In addition to the outer and inner sections, each heater element can further comprise at least one intermediate section arranged in series to the outer and inner sections. In this case the hotplate comprises at least one intermediate region located between said outer and inner regions, wherein the intermediate sections of the heater elements are arranged in the intermediate region of the hotplate. This allows further versatility for controlling the radial temperature profile when designing the heater structure.

Advantageously, the intermediate section has an electrical cross section smaller than the inner section because it is located radially outward from the inner section. In a particularly advantageous embodiment, it has the same cross section as the outer section (with "the same" describing an equality within 10% or better).

In another embodiment, the intermediate section has an electrical cross section different from the cross section of the outer section. In particular, the electrical cross section of the intermediate section can be between the cross section of the outer and the inner sections.

In this case, each segment of the hotplate advantageously comprises an intermediate segment region formed by the intersection of said segment with the intermediate region. The intermediate section of each heater element is arranged in one of the intermediate segment regions, with each intermediate segment region receiving the intermediate section of exactly one heater element.

Similar as above, in this case, the intermediate section of each heater element can be arranged in a segment different from the inner and/or outer section of said heater element, and/or it can be arranged in the same segment as the inner and/or outer section of said heater element.

In one embodiment, each inner section comprises a first conducting lead, a second conducting lead and a plurality of conductors extending electrically in parallel between said first and second conducting leads. By splitting the inner section into a plurality of conductors arranged electrically in parallel, the heat from the inner section can be spread over a larger area. In addition, the widths of the conductors can be kept small, which makes them more amenable to manufacturing using a damascene process.

Other advantageous embodiments are listed in the dependent claims as well as in the description below.

BRIEF DESCRIPTION OF THE DRAWINGS

The invention will be better understood and objects other than those set forth above will become apparent from the following detailed description thereof. Such description makes reference to the annexed drawings, wherein.

MODES FOR CARRYING OUT THE INVENTION

Definitions

The present invention is best described in geometrical terms, such as circles, arcs or radial lines. It must be noted, however, that the relevant properties of the device are its thermal properties, and thermal properties do not drastically change upon small deviations from an ideal geometry. Hence, small deviations from a mathematically strict interpretation of the geometric properties still remain within the scope of the invention. The following definitions illustrate this.

The term "circular arc" designates a segment of the circumference of a circle. A section of a heater element (or any other similar element) is understood to "extend along a circular arc" if there is a circular arc such that the closest distance from each point on the center line of the heater element to this circular arc is within less than 10%, in particular within less than 5%, of the diameter of the circle defining the circular arc.

Similarly, a hotplate or membrane is understood to "be circular" if there is a circle such that the closest distance from each point on the peripheral rim of the hotplate or membrane to this circle is less than 10%, in particular less than 5%, of the diameter of the circle.

A conducting lead is understood to be "extending radially" on a hotplate if the closest distance from each point on the center line of the electrical lead to a radial line of the hotplate is less than 10%, in particular less than 5%, of the diameter of the hotplate.

A "segment" of the hotplate designates a continuous area of the hotplate that extends from the center of the hotplate all the way to the periphery thereof. The shape of the segment must further be such that the hotplate can be completely divided into N segments of such shape, with said N segments being arranged around the center of the hotplate with an N-fold rotational symmetry. The dividing lines between the segments, which extend from the center to the periphery, can be straight, radial lines, or they can e.g. be curved. A section of a heater element is understood to lie in a segment if at least 90%, in particular at least 95%, of said section lies within said segment.

Similarly, if it is said that e.g. the heater structure has N-fold rotational symmetry, small local deviations from said symmetry that do not give rise to substantial thermal effects can be disregarded.

Figure 1:
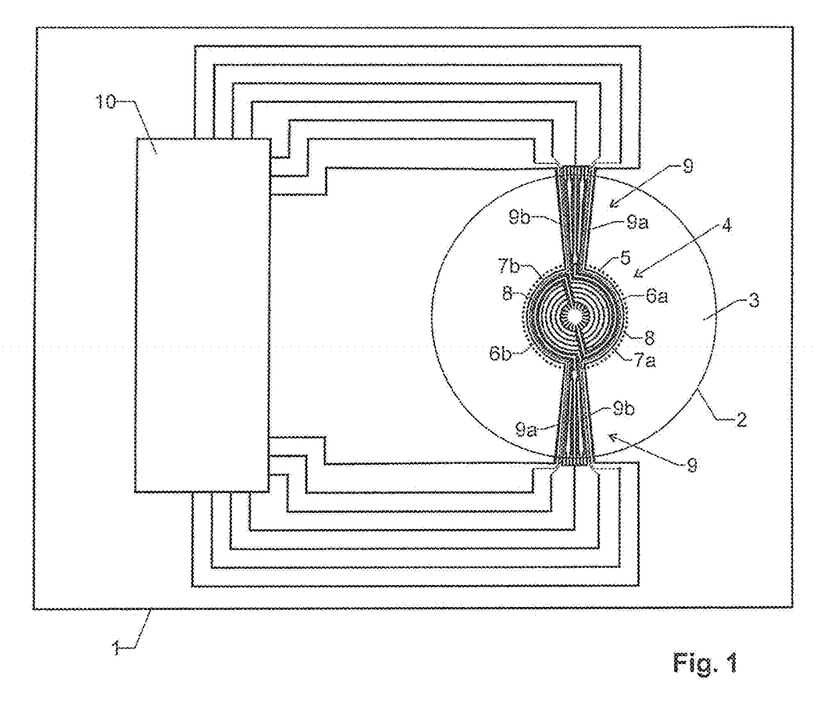
FIG. 1 is a schematic representation of the components of a sensor device.

Sensor Device:

FIG. 1 shows a sensor device having a substrate 1, in particular a substrate of silicon. Substrate 1 has an opening or recess 2 arranged therein, with a dielectric membrane 3 extending over at least part of opening or recess 2. This type of structure is known to the skilled person and e.g. described in EP 2278308 or WO 2014/012948.

Membrane 3 carries a hotplate 4, which generally designates a heatable area. A sensing structure 5, such as a metal oxide layer and electrodes for measuring the resistance of said layer, is arranged on hotplate 4. Suitable sensing structures are known to the skilled person and e.g. described in the references mentioned above.

As can be seen, hotplate 4 as well as membrane 3 are circular, and hotplate 4 is arranged in the center of membrane 3. This design minimizes mechanical stress in the structure. Hotplate 4 is comparatively small compared to membrane 3 in order to reduce the thermal flow from hotplate 4 to the bulk of substrate 1. Advantageously, the distance between the outer rim of hotplate 4 to the periphery of membrane 3 is at least 50% of the radius of membrane 3.

As will be described in more detail below, hotplate 4 carries a heater structure comprising N heater elements 6a, 6b and N optional auxiliary heaters 7a, 7b, with N being an integer (see also FIG. 2). N is typically between 2 and 4, but it may be larger, and in the embodiment of FIG. 1 we have N=2.

Further, hotplate 4 comprises a substantially circular temperature sensor 8.

Bundles 9 of electrical supply lines 9a, 9b for the heater structure extend between the periphery of membrane 3 and the outer rim of hotplate 4. Advantageously, the number of these bundles 9 is equal to the number N.

FIG. 1 further shows a driver 10 for generating a heating current through the heater structure. Driver 10 is advantageously formed by circuitry integrated on substrate 1, but it may also be formed by external circuitry. It is adapted to generate heater currents through the heater structure. Typically, it is adapted to operate the heater elements 6a, 6b in parallel by applying them to a common heating voltage. This voltage can be comparatively low, in particular less than 2 Volts.

Driver 10 is further adapted to operate the auxiliary heaters 7a, 7b and to evaluate the signal from temperature sensor 8.

Figure 2:
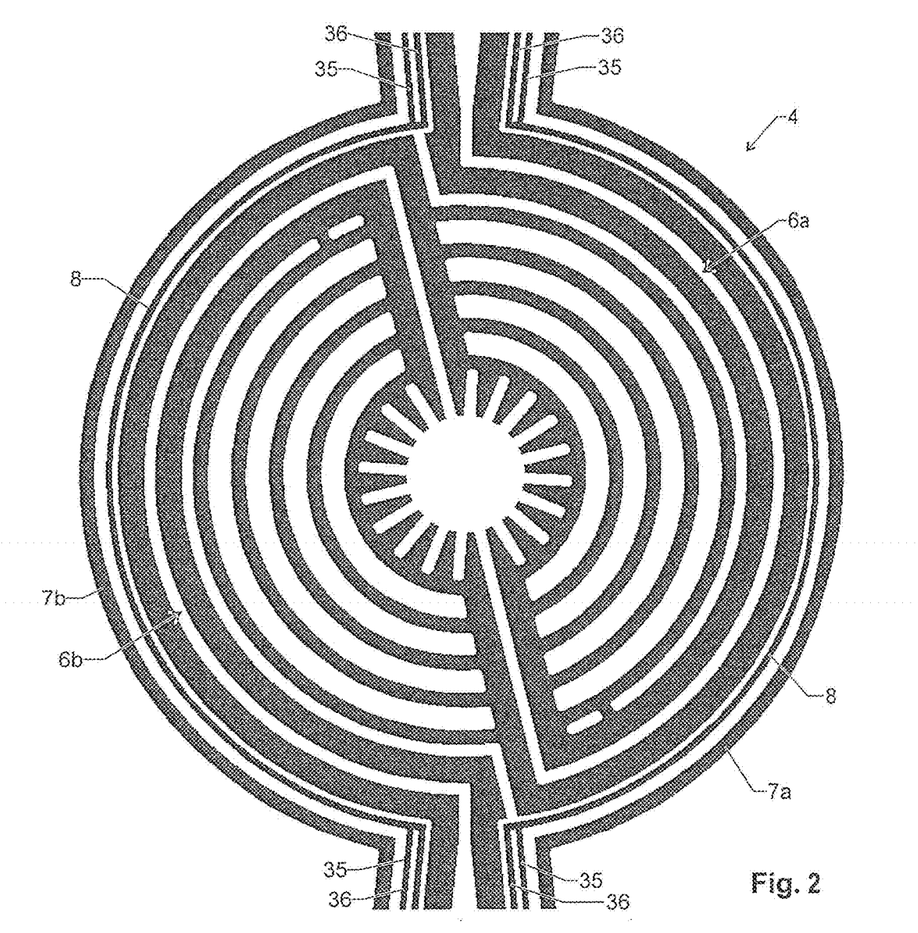
FIG. 2 shows the hotplate and its associated components in more detail.
Figure 3:
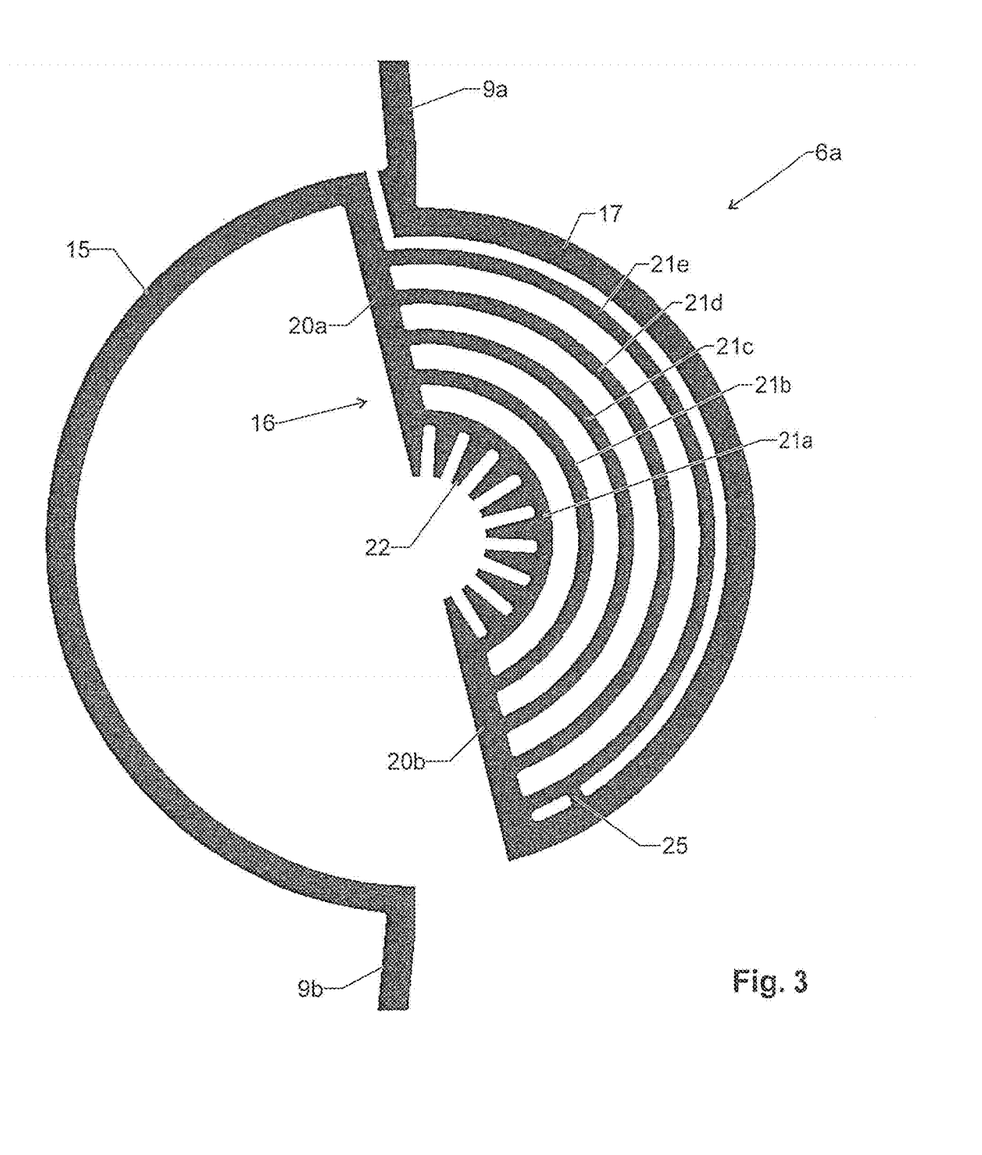
FIG. 3 shows a single heater element of the embodiment of FIG. 2.

Hotplate Design:

FIGS. 2 and 3 illustrate an advantageous design of hotplate 4 in more detail, with FIG. 2 showing all the components of the heater structure, while FIG. 3 shows a single heater element 6a only.

The black parts of FIGS. 2 and 3 show the metallic section of a single metal layer. In an advantageous embodiment, this metal layer is a wolfram metal layer structured in a damascene process. However, the metal layer can e.g. also be a platinum metal layer and it can be manufactured using an etching process.

As mentioned, the heater structure comprises N heater elements 6a, 6b, with N=2 in the embodiment shown. In order to obtain symmetric temperature distribution in the hotplate, the shown heater elements 6a, 6b form a pattern that is rotationally symmetric in view of the center of hotplate 4. Further, the whole heater structure is rotationally symmetric in view of the center of hotplate 4. The symmetry is N-fold.

As can best be seen from FIG. 3, a single heater element 6a comprises an outer section 15, a center section 16 as well as an intermediate section 17. The sections 15, 16, 17 are arranged electrically in series between the supply lines 9a, 9b. In the embodiment of FIG. 3, inner section 16 is electrically arranged between outer section 15 and intermediate section 17, i.e. the current flows from outer section 15 into inner section 16 and then into intermediate section 17, or vice versa.

Center section 16 in turn comprises a first and a second conducting lead 20a, 20b as well as a plurality of conductors 21a-21e that extend, electrically arranged in parallel, between the conducting leads 20a, 20b. In the shown embodiment, the conducting leads 20a, 20b extend radially in hotplate 4, while the conductors 21a-21e are strip-shaped and arcuate. In particular, the conductors 21a-21e form circular arcs concentric to the center of hotplate 4.

In addition, and as seen in FIG. 3, the conducting lead 21a that is closest to the center of hotplate 4 comprises a plurality of equidistant, metallic fingers 22 that extend radially towards the center. These fingers act as heat spreaders and improve the thermal homogeneity in the central area of hotplate 4.

First conducting lead 20a is connected to outer section 15 and second conducting lead 20b is connected to intermediate section 17 of the same heater element.

As mentioned above, the design of the inner section 16 of FIG. 3 is particularly suited for being manufactured in a damascene process. This is because all of the metallic regions are comparatively small at least along one direction, which helps to avoid or at least reduce a "dishing" effect that leads to a decreased thickness in the center of a structure manufactured in a damascene process.

As can be seen from FIGS. 1-3, this also applies to the outer and intermediate sections, where the metallic regions are comparatively small at least along one direction.

For the same reason, the leads of the bundles 9 of supply lines are branching, as shown in FIG. 1, as they extend outwards from hotplate 4. This reduces their resistance while keeping the width of the leads small in order to reduce dishing effects.

Advantageously, the maximum width of a conducting lead of the heater structure is less than 12 μm, in particular less than 10 μm, to avoid dishing. In order to obtain a stable damascene process, it has been found that the minimum distance between neighbouring conducting leads should be at least 1 μm.

Figure 4:
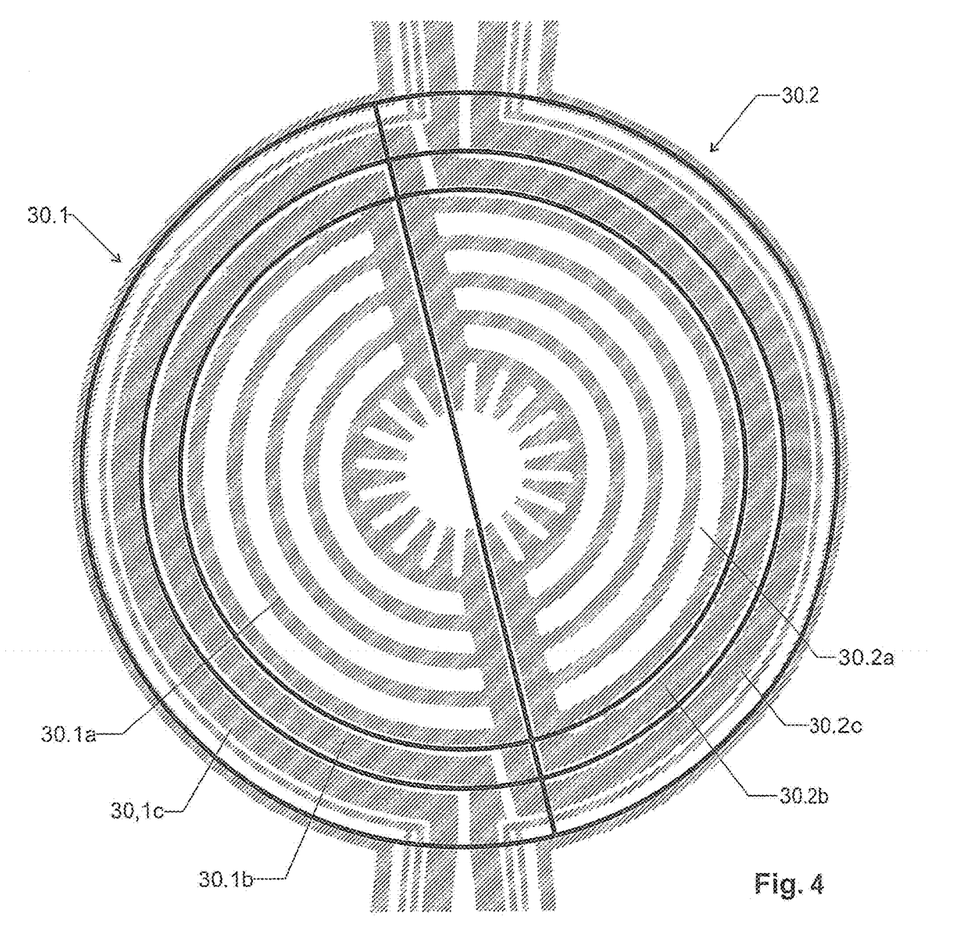
FIG. 4 illustrates the segments of the hotplate.

The heater structure can be better understood when dividing hotplate 4 into individual segments and regions as shown in FIG. 4. In this figure, hotplate 4 of FIG. 2 is divided into two segments 30.1, 30.2. (In general, for a heating structure of symmetry N, the number of segments is equal to N.) The segments have equal shape and extend from the center of hotplate 4 to its periphery. Each segment is divided into an inner segment region 30.1a, 30.2a, an intermediate segment region 30.1b, 30.2b and an outer segment region 30.1c, 30.2c.

In addition, hotplate 4 can also be divided into circular and annular regions. A circular inner region consists of the combined area of all inner segment regions 30.1a and 30.2a, an annular intermediate region consists of the combined area of all intermediate segment regions 30.1b and 30.2b and an annular outer region consists of the combined area of all outer segment regions 30.1c, 30.2c. The outer region 30.1c+30.2c surrounds both the intermediate region 30.1b+30.2b and the inner region 30.1a+30.2a, and the intermediate region 30.1b+30.2b surrounds the inner region 30.1a+30.2a.

In other words, the inner segment regions 30.1a, 30.2a are formed by the intersection of the respective segments 30.1, 30.2 with the inner region of hotplate 4, the intermediate segment regions 30.1b, 30.2b are the intersection of the respective segments 30.1, 30.2 with the intermediate region of hotplate 4, and the outer segment regions 30.1c, 30.2c are the intersection of the respective segments 30.1, 30.2 with the outer region of hotplate 4.

The outer sections 15 of all heater elements 6a, 6b are arranged in the outer region 30.1c+30.2c. The intermediate sections 17 of all heater elements 6a, 6b are arranged in the intermediate region 30.1b+30.2b, and the inner sections 16 of all heater elements 6a, 6b are arranged in the inner region 30.1a+30.2a.

As can also be seen for the embodiment shown in FIGS. 2-4, each heater element 6a, 6b extends over two neighbouring segments 30.1, 30.2. This helps to avoid sharp turns and in particular U-turns in the electrically conducting leads. Such turns lead to regions of increased current density and therefore to undesired hotspots. In the general case of N heater elements, each heater element extends over at least two neighbouring segments of the hotplate.

In the embodiment of FIG. 2-4, the outer section 15 of each heater element is arranged in a segment different from the inner and intermediate sections 16, 17. In other words, the inner section 16 and the intermediate section 17 of one segment both belong to the same heater element, but the outer section 15 in each segment belongs to a different heater element than the intermediate and inner sections of said segment. For example, the outer section in segment 30.2 belongs to heater element 6b, while the inner and intermediate sections in segment 30.2 belong to heater element 6a.

Some alternative embodiments of the heater elements will be described below.

In order to obtain a homogeneous temperature distribution over hotplate 4, the heating power per surface area must not be uniform because thermal losses increase towards the outer rim of the hotplate.

The heating power per volume in a conductor of the heating structure is basically given by $j^2 \cdot \rho$, with j being the current density and ρ the resistivity of the conductor. Since the resistivity as well as the thickness (height) are advantageously the same for all conductors of the heating structure, the main parameter for influencing the heating power in the conductors is the current density j. This current density j primarily depends on the conductor geometry, in particular the width (if the height is not varied) of the conductors as well as the manner in which the conductors are branching and (in particular for parallel conductors) the lengths of the individual conductors. The average heating power per surface area, when averaged over a unit area that has dimensions considerably larger than the width of the conductors, further depends on the ratio of area covered by the conductors vs. the unit area. The exact distribution of the heating power and the temperature distribution can be assessed using finite element calculus.

For a single heater element, such as heater element 6a of FIG. 3, the total current in all three sections 15, 16 and 17 is equal because the sections are arranged in series. However, a section that has a large electrical cross section shows lower current density and therefore lower heat generation per surface area than a section that has a small electrical cross section. In this context, the term "cross section" defines the cross section of the metallic conductor of each section perpendicular to the flow of the current. For the outer and intermediate sections 15 and 17 of FIG. 3, this cross section is equal to the product of width×height of the electrical leads. In the inner section 16, which contains several parallel conductors 21a-21e, the cross section is the sum of the cross sections of the parallel conductors.

Further, the heating power per surface area also depends on the distance between (i.e. the density of) the various metallic conductor leads in a given surface area.

In order to have a high heat generation in the outer region 30.1c+30.2c, the outer sections 15 of the heating elements 6a, 6b have smaller electrical cross section than the inner sections 16. Further, the distances between individual metallic leads of the heater elements 6a, 6b are, in the shown embodiment, smaller in the outer and intermediate regions 30.1c+30.2c, 30.1b+30.2b than in the inner region 30.1a+30.2a.

The average heating power per surface area depends, as mentioned, on a variety of factors and has to be calculated using numerical methods. However, advantageously the maximum electrical cross section of the outer section 15 will generally be smaller than the maximum electrical cross section of the inner section 16. In this context, the "maximum" cross section is the largest electrical cross section (in the sense above) that can be found for a given section of the heater element.

In the embodiment of FIG. 2-4, the cross sections of the outer section 15 and the intermediate section 17 of each heating element 6a, 6b are equal. However, if an even higher heat generation is desired in outer region 30.1c+30.2c, the cross section of the outer section 15 can be smaller than the cross section of the intermediate section 17.

In the shown embodiment, each heater element is shown to have a shunt lead 25 (see FIG. 3), which (in addition to the connecting leads 20a, 20b) interconnects intermediate section 17 to an outmost one 21e of the arcuate conductors 21a-21e. This shunt lead 25, which is closer, in particular at least 2 times, in particular at least 10 times, closer, to second connecting lead 20b than to first connecting lead 20a, reduces the current density at the radially outward end of second conducting lead 20b, which in turn reduce a potential overheating at that location.

FIG. 2 further shows the auxiliary heaters 7a, 7b. Each auxiliary heater extends in a circular arc along the periphery of hotplate 4. It has an electrical cross section smaller than the one of the outer sections 15 of the heater elements 6a, 6b. As mentioned, the auxiliary heaters 7a, 7b are optional. They can be used either to improve the homogeneity of the temperature distribution at the periphery of hotplate 4, or to achieve higher temperatures in hotplate 4.

If there are N heater elements in hotplate 4, the number of additional heaters is advantageously also equal to N in order to simplify the design of the supply leads.

Finally, FIG. 2 shows the temperature sensor 8, which, in the shown embodiment, is a structure separate from the heating structure. It extends in two circular arcs along the periphery of hotplate 4. In more general terms, if there are N heater elements, temperature sensor 8 advantageously extends in N circular arcs along the periphery of the hotplate. Assuming that there is a residual radial inhomogeneity of the temperature distribution on hotplate 4, the arrangement of temperature sensor 8 as N circular arcs extending along the hotplate's periphery places the sensor in a region of constant temperature, which allows to derive an accurate temperature value.

Two leads 35, 36, which extend between hotplate 4 and the periphery of membrane 3, are attached to each end of each circular arc of temperature sensor 8, one for carrying a current and the second for measuring the voltage drop over each arc. This allows to implement a four point measurement of the temperature-dependent electrical resistance of each arc.

Further Embodiments

The embodiment of FIGS. 2-4 shows only one of various ways for designing the heater elements.

For example and as mentioned, the number N of heater elements can vary. While the inner, intermediate and outer sections 16, 17 and 15 of each of the two heaters of FIGS. 2-4 extend over an angular region of approximately 180° of the hotplate, the heater structure can also be designed to have e.g. N=3 heaters, whose inner, intermediate and outer sections only extend over approximately 120° of the hotplate. In this case, hotplate 4 comprises three segments, with each segment extending also over 120° of the hotplate. Three bundles 9 of electrical supply lines are provided at regular angular intervals between hotplate 4 and the outer edge of membrane 3. The intermediate and inner sections 17, 16 of each heater element are located in one segment of hotplate 4, while the outer section 15 extends along the periphery of a neighbouring segment.

A similar design can be adopted for N=4, where each segment covers only 90° of the hotplate and four bundles 9 of electrical supply lines are used to feed the heater elements. N can even be a higher number.

Figures 5, 6:
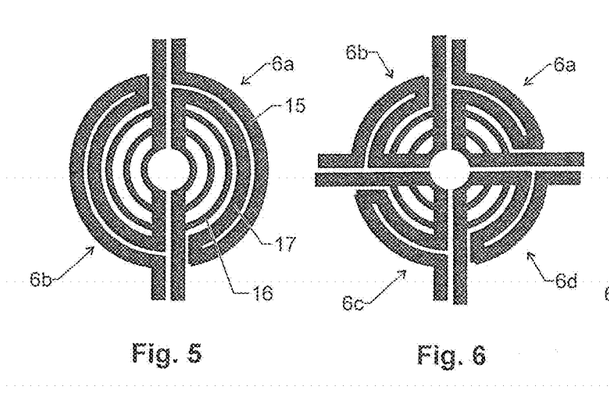
FIG. 5 is a schematic representation of a second embodiment of the heater structure.
FIG. 6 is a schematic representation of a third embodiment of the heater structure and FIG. 7 is a schematic representation of a fourth embodiment of the heater structure.

FIG. 5 shows a further embodiment of the heater elements with N=2. In this case, the inner, intermediate and outer sections 16, 17 and 15 of each heater element 6a, 6b reside in the same segment of hotplate 4. This is achieved by electrically arranging intermediate section 17 between inner section 16 and outer section 15 as shown in the figure.

FIG. 6 shows the same design as FIG. 5 but for a symmetry N=4 and therefore with four heater elements 6a, 6b, 6c, 6d. Similar designs are readily implemented for N=3 or other values.

Figure 7:
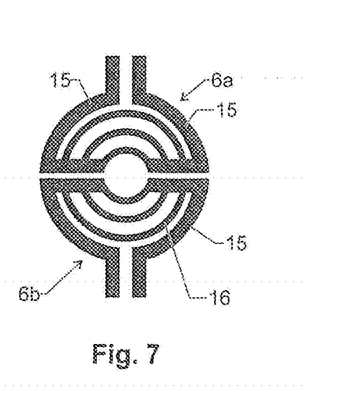

FIG. 7 shows a design of heater elements 6a, 6b lacking the intermediate section 17, and it has two shorter outer sections 15. When looking at the average heating power (averaged over a surface area having a size considerably larger than the width of the conductors), this design provides less heating power per surface area at the periphery of hotplate 4 and can make sense in cases where radial heat losses of hotplate 4 are small.

Notes:

As mentioned above, hotplate 4 is advantageously circular in order to obtain a highly symmetric temperature distribution. The present invention is, however, not limited thereto, and hotplate 4 can also take other shapes. For example, hotplate 4 can have the shape of a regular polygon, in particular a regular polygon whose vertices lie on a common circle. In this case, the number n of vertices can be any number lager than 2, but advantageously n is at least 6 for a more even temperature distribution.

The present design is, as mentioned, well suited for achieving high temperatures even for low supply voltages. In particular, the design of the heating structure is such that a temperature of at least 350° C. can be achieved with a supply voltage of less than 3V, in particular less than 2V, in particular less than 1.5V, applied over each heater element.

While there are shown and described presently preferred embodiments of the invention, it is to be distinctly understood that the invention is not limited thereto but may be otherwise variously embodied and practiced within the scope of the following claims.

The invention claimed is:

1. A sensor device comprising
a substrate having a hotplate, wherein said hotplate comprises an inner region and an outer region, wherein said outer region surrounds said inner region,
a heater structure arranged in said hotplate,
a driver for generating a heating current through said heater structure, and
a sensing structure arranged on said heater structure,
wherein said heater structure comprises a number N>1 of resistive heater elements, with each of said heater elements comprising an outer section and an inner section electrically arranged in series, and wherein said driver is structured and adapted to heat said heater elements with parallel currents,
wherein a maximum electrical cross section of said outer section is smaller than a maximum electrical cross section of said inner section such that the current densities in the outer sections are larger than in the inner sections,
wherein said outer sections are arranged in the outer region of said hotplate and said inner sections are arranged in the inner region of said hotplate, and
wherein each inner section comprises a first conducting lead, a second conducting lead and a plurality of conductors extending electrically in parallel between said first and second conducting leads.

2. The sensor device of claim 1 wherein said hotplate has N segments of equal shape, with each segment extending from a center of said hotplate to a periphery of said hotplate and,
wherein each segment has an inner segment region formed by an intersection of said segment with said inner region and an outer segment region formed by an intersection of said segment with said outer region.

3. The sensor device of claim 2, wherein at least one of the following conditions (a) and (b) obtains:
(a) the inner section of each heater element is arranged in one of said inner segment regions, with each inner segment region receiving the inner section of one heater element;
(b) the outer section of each heater element is arranged in one of said outer segment regions, with each outer segment region receiving the outer section of one heater element.

4. The sensor device of claim 3, wherein the outer section of each heater element is arranged in a segment different from the inner section of said heater element or
wherein the outer section of each heater element is arranged in the same segment as the inner section of said heater element.

5. The sensor device of claim 1, wherein each heater element further comprises at least one intermediate section arranged in series to said outer and said inner sections,
wherein said hotplate comprises at least one intermediate region located between said outer and inner regions, and
said intermediate sections are arranged in the intermediate region of said hotplate.

6. The sensor device of claim 5, wherein said intermediate section has an electrical cross section smaller than said inner section and in particular equal to said outer section.

7. The sensor device of claim 5,
wherein said hotplate has N segments of equal shape, with each segment extending from a center of said hotplate to a periphery of said hotplate and,
wherein each segment has an inner segment region formed by an intersection of said segment with said inner region and an outer segment region formed by an intersection of said segment with said outer region,
wherein each segment has an intermediate segment region formed by an intersection of said segment with said intermediate region,
and wherein the intermediate section of each heater element is arranged in one of said intermediate segment regions, with each intermediate segment region receiving the intermediate section of one heater element.

8. The sensor device of claim 7, wherein the intermediate section of each heater element is arranged in a segment different from at least one of the inner and outer sections of said heater element.

9. The sensor device of claim 7 wherein the intermediate section of each heater element is arranged in the same segment as at least one of the inner and outer sections of said heater element.

10. The sensor of claim 7 wherein the inner section and the intermediate section in each segment belong to a same one of said heater elements, but the outer section in each segment belongs to a different heater element than the heater element to which the intermediate and inner sections of said segment belong.

11. The sensor of claim 6 wherein said inner section is electrically arranged between said outer section and said intermediate section.

12. The sensor device of claim 1 wherein at least one of the following conditions (a) and (b) obtains:
(a) said first and second conducting leads extend radially in said hotplate;
(b) said conductors are strip-shaped and arcuate, in particular wherein said conductors form circular arcs.

13. The sensor of claim 12, wherein a conducting lead closest to a center of said hotplate comprises metallic fingers radially extending towards said center.

14. The sensor device of claim 1,
wherein the intermediate section of each heater element has an electrical cross section smaller than the inner section of that heater element and in particular equal to the outer section of that heater element and
wherein the first conducting lead of the inner section of each heater element is connected to the outer section of that heater element and the second conducting lead of that inner section is connected to the intermediate section of that heater element.

15. The sensor device of claim 14 wherein each heater element comprises at least one shunt lead, in addition to said conducting leads, that connects said intermediate section to an outmost one of said conductors, wherein said shunt lead is closer to said second conducing lead than to said first conducting lead.

16. The sensor device of claim 1 wherein N=2.

17. The sensor device of claim 1 wherein said hotplate is circular.

18. The sensor of claim 1, wherein said hotplate is shaped as a regular polygon with n vertices, wherein said n vertices lie on a common circle, and in particular wherein n is at least 6.

19. The sensor device of claim 1 wherein said substrate comprises an opening or recess and a membrane spanning said opening or recess,
wherein said membrane is circular,
wherein said hotplate is circular and arranged in a center of said membrane,
wherein a distance between an outer rim of said hotplate and a periphery of said membrane is at least 50% of a radius of said membrane, and
wherein said sensor device has exactly N bundles of electrical supply lines for said heater structure running between the periphery of said membrane and the outer rim of said hotplate.

20. The sensor device of claim 1 further comprising a temperature sensor, in addition to said heater structure, extending in N circular arcs along a periphery of said hotplate.

21. The sensor device of claim 1 wherein said heater structure further comprises, in addition to said heater elements, N auxiliary heaters extending in circular arcs along a periphery of said hotplate.

22. The sensor device of claim 1 wherein said heater structure is rotationally symmetric with N-fold symmetry in view of a center of said hotplate.

23. The sensor device of claim 1 wherein at least one of the following conditions (a) and (b) obtains:
   (a) a maximum width of any conducting lead of the heater structure is less than 12 µm, in particular less than 10 µm;
   (b) the minimum distance between any neighbouring conducting leads is at least 1 µm.

24. A sensor device comprising
a substrate having a hotplate, wherein said hotplate comprises an inner region and an outer region, wherein said outer region surrounds said inner region,
a heater structure arranged in said hotplate,
a driver for generating a heating current through said heater structure, and
a sensing structure arranged on said heater structure,
wherein said heater structure comprises a number N>1 of resistive heater elements, with each of said heater elements comprising an outer section and an inner section electrically arranged in series, and wherein said driver is structured and adapted to heat said heater elements with parallel currents,
wherein a maximum electrical cross section of said outer section is smaller than a maximum electrical cross section of said inner section,
wherein said outer sections are arranged in the outer region of said hotplate and said inner sections are arranged in the inner region of said hotplate,
wherein each inner section comprises a first conducting lead, a second conducting lead and a plurality of conductors extending electrically in parallel between said first and second conducting leads,
wherein at least one of the following conditions (a) and (b) obtains:
   a) said first and second conducting leads extend radially in said hotplate;
   b) said conductors are strip-shaped and arcuate, in particular wherein said conductors form circular arcs; and
wherein a conducting lead closest to a center of said hotplate comprises metallic fingers radially extending towards said center.

* * * * *